United States Patent
Hansen et al.

(10) Patent No.: US 9,314,581 B2
(45) Date of Patent: Apr. 19, 2016

(54) LARYNGEAL MASK WITH A BITE ABSORBING CONNECTOR

(71) Applicant: Ambu A/S, Ballerup (DK)

(72) Inventors: Jan Guldberg Hansen, Greve (DK); Troels Nicolaj Qvist, Roskilde (DK); Peer Hoffmann, Stenlose (DK); Erik Ollgaard Vilhelmsen, Espergaerde (DK); Lasse Kjeld Gjoske Petersen, Frederiksvaerk (DK)

(73) Assignee: AMBU A/S, Ballerup (DK)

(*) Notice: Subject to any disclaimer, the term of this patent is extended or adjusted under 35 U.S.C. 154(b) by 0 days.

(21) Appl. No.: 14/266,879

(22) Filed: May 1, 2014

(65) Prior Publication Data

US 2015/0209538 A1 Jul. 30, 2015

(30) Foreign Application Priority Data

Jan. 24, 2014 (DK) .................................. 2014 70034

(51) Int. Cl.
*A61M 16/04* (2006.01)
*A61M 16/08* (2006.01)

(52) U.S. Cl.
CPC ....... *A61M 16/0493* (2014.02); *A61M 16/0409* (2014.02); *A61M 16/0816* (2013.01); *A61M 16/0415* (2014.02)

(58) Field of Classification Search
CPC .......... A61M 16/0488; A61M 16/049; A61M 16/0493; A61M 16/0495; A61M 16/0497; A61M 16/04; A61M 16/0402; A61M 16/0409; A61M 16/0415; A61M 16/0427; A61M 16/0463; A61M 16/0475; A61C 17/02; A61C 17/04; A61C 17/043; A61F 5/56; A61F 5/566; A63B 2071/086; A63B 71/085

USPC ............ 128/207.14–207.17, 200.24, 201.26, 128/206.29, 861, 862, 848; 433/91–96, 229
See application file for complete search history.

(56) References Cited

U.S. PATENT DOCUMENTS 3,874,377 A * 4/1975 Davidson ................. 128/207.15
4,068,658 A 1/1978 Berman
(Continued)

FOREIGN PATENT DOCUMENTS

AU 647437 B2 3/1994
EP 1043039 10/2000
(Continued)

OTHER PUBLICATIONS

Search Report of the Danish Patent and Trademark Office in Application No. PA 2014 70034, completed Apr. 7, 2014, 4 pages.
(Continued)

*Primary Examiner* — Tan-Uyen (Jackie) T Ho
*Assistant Examiner* — Mark K Han
(74) *Attorney, Agent, or Firm* — Faegre Baker Daniels LLP

(57) ABSTRACT

A laryngeal mask insertable into a patient, an airway tube of the laryngeal mask having a bore extending from a proximal to a distal end of the airway tube, a connector provided at the proximal end of the airway tube, the connector comprising a connector body with a longitudinal bore, at least two wall portions extending longitudinally from a first continuous wall to a second continuous wall, and two parallel and opposite longitudinal wall cut-away portions intermediate the at least two wall portions, the length of the longitudinal wall cut-away portions being greater than the length of the first continuous wall.

23 Claims, 3 Drawing Sheets

(56) References Cited

U.S. PATENT DOCUMENTS

| | | | |
|---|---|---|---|
| 4,069,820 | A | 1/1978 | Berman |
| 4,166,467 | A | 9/1979 | Abramson |
| 4,166,468 | A * | 9/1979 | Haynie .................... 128/207.15 |
| 4,198,970 | A | 4/1980 | Luomanen |
| 4,338,930 | A | 7/1982 | Williams |
| 4,683,879 | A | 8/1987 | Williams |
| 4,827,910 | A | 5/1989 | Mathews, III |
| 4,995,388 | A | 2/1991 | Brain |
| 5,241,956 | A | 9/1993 | Brain |
| 5,318,017 | A | 6/1994 | Ellison |
| 5,460,176 | A | 10/1995 | Frigger |
| 5,655,519 | A | 8/1997 | Alfery |
| 5,865,176 | A | 2/1999 | O'Neil |
| 6,196,224 | B1 | 3/2001 | Alfery |
| 6,338,343 | B1 | 1/2002 | Augustine et al. |
| 6,386,199 | B1 | 5/2002 | Alfery |
| 6,474,332 | B2 | 11/2002 | Arndt |
| 6,606,991 | B2 | 8/2003 | Chou |
| 6,749,606 | B2 | 6/2004 | Keast et al. |
| 6,830,049 | B2 | 12/2004 | Augustine et al. |
| 6,974,321 | B2 * | 12/2005 | Hirsch ..................... A61C 5/14 433/140 |
| 6,983,744 | B2 | 1/2006 | Alfery |
| 7,004,169 | B2 | 2/2006 | Brain |
| 7,013,899 | B2 | 3/2006 | Alfery et al. |
| 7,097,802 | B2 | 8/2006 | Brain |
| 7,134,431 | B2 * | 11/2006 | Brain ....................... 128/200.26 |
| 7,159,589 | B2 | 1/2007 | Brain |
| 7,866,313 | B2 | 1/2011 | Isenberg et al. |
| 7,878,201 | B2 | 2/2011 | Mongeon |
| 8,215,307 | B2 | 7/2012 | Nasir |
| 8,257,413 | B2 | 9/2012 | Danek et al. |
| 2003/0037789 | A1 | 2/2003 | Klinberg et al. |
| 2008/0041391 | A1 | 2/2008 | Worley |
| 2008/0276936 | A1 | 11/2008 | Cook |
| 2010/0242957 | A1 | 9/2010 | Fortuna |
| 2011/0126840 | A1 | 6/2011 | Ogilvie |
| 2011/0203594 | A1 | 8/2011 | Brain |
| 2012/0247477 | A1 | 10/2012 | Stephenson et al. |
| 2013/0247917 | A1 | 9/2013 | Brain |

FOREIGN PATENT DOCUMENTS

| | | |
|---|---|---|
| EP | 2108396 | 10/2009 |
| GB | 2319182 A | 5/1998 |
| GB | 2438799 | 5/2007 |
| GB | 2465453 | 9/2009 |
| WO | WO 2007/071429 | 7/2007 |
| WO | WO 2010/058220 | 5/2010 |
| WO | WO 2012/042218 | 4/2012 |
| WO | WO 2012/042219 | 4/2012 |

OTHER PUBLICATIONS

Search Report of the European Patent Office in counterpart EP Application No. 14196137.5, completed Apr. 28, 2015, 5 pages.

* cited by examiner

LARYNGEAL MASK WITH A BITE ABSORBING CONNECTOR

CROSS-REFERENCE TO RELATED APPLICATIONS

This application claims the benefit of priority, under 35 U.S.C. §119, of Danish Patent Application No. PA 2014 70034, filed Jan. 24, 2014, the disclosure of which is expressly incorporated herein by reference in its entirety.

FIELD OF THE APPLICATION

The present invention relates to a laryngeal mask with a bite absorbing connector and a bite absorbing connector for a laryngeal mask.

BACKGROUND

It is well known in the art of artificial airway devices such as laryngeal masks to provide a connector at the proximal end of the airway tube for allowing connection of the artificial breathing device to a breathing apparatus. It is recognized that anesthetised patients may bite the airway tube of a laryngeal mask, because a portion of the airway tube inevitably is located at the inter-dental gap, i.e. the teeth of the patient contact the proximal end of the airway tube at a point of tooth contact. Since most airway tubes of laryngeal masks are made flexible to facilitate insertion and comfort to the patient, a patient biting the airway tube may therefore result in a collapse of the most common type of airway tubes and in dental damages if the airway tube is made too rigid at the point of tooth contact.

The publication WO 2007/071429 discloses a connector for a laryngeal mask, which connector comprises a connector body, a flange extending radially from the connector body, and an insertion section adapted for insertion into the bore at the proximal end of an airway tube of the laryngeal mask to support the airway tube in use, the insertion section including a continuous wall extending longitudinally from the flange. To reinforce a portion of the airway tube two wall portions extend longitudinally from the continuous wall and two parallel and opposite longitudinal wall cut-away portions are intermediate the at least two wall portions. Thereby, the connector performs dual functions as the connector besides from being an adaptor to a breathing device also prevents the airway tube from collapsing if the patient bites it. However, it may be difficult to easily secure the insertion section of the connector into the airway tube and ensure that no leaks occur between the insertion section and the airway tube during ventilation of the patient.

A connector of the above-mentioned known kind is utilized in the publication WO 2012/042219, which discloses a more complex solution wherein the connector forms part of the airway tube, which is configured to substantially maintain the bore of the airway tube at the point of tooth contact.

SUMMARY

In view of the above it is an object of the invention to provide a bite absorbing connector which is easy to mount in an air tight matter in the airway tube of a laryngeal mask.

This object is achieved by a laryngeal mask insertable into a patient, an airway tube of the laryngeal mask having a bore extending from a proximal to a distal end of the airway tube, the airway tube configured such that in use, the teeth of the patient contact the proximal end at a point of tooth contact, a connector provided at the proximal end of the airway tube, the connector comprising: a connector body with a longitudinal bore, a flange extending radially from the connector body, and an insertion section adapted for insertion into the bore at the proximal end of the airway tube to support the airway tube in use, the insertion section including a first continuous wall extending longitudinally from the flange, at least two wall portions extending longitudinally from the first continuous wall to a second continuous wall, and two parallel and opposite longitudinal wall cut-away portions intermediate the at least two wall portions, the length of the longitudinal wall cut-away portions being greater than the length of the first continuous wall, the at least two wall cut-away portions configured to reduce support of the airway tube for allowing local deformation of the airway tube at the point of tooth contact upon application of pressure by the patient's teeth, whilst preventing the airway tube from a full collapse. The configuration with a second distal continuous wall has the advantage of providing an improved fit between the insertion section of the connector and the airway tube, and allows the connector to serve as a bite absorber at the point of tooth contact so as to prevent damages of the patient's teeth.

In a practically preferred embodiment the at least two cut-away portions are positioned on opposing sides of a ventral-dorsal plane of the laryngeal mask.

In a further practically preferred embodiment the at least two cut-away portions are positioned on opposing sides of a left-right plane of the laryngeal mask.

In an even further embodiment at least two cut-way portions are positioned on each side of a left-right plane of the laryngeal mask. This embodiment has shown to be especially advantageous for laryngeal masks configured to allow intubation of an endotracheal tube via the bore of the airway tube, because the configuration with two by two opposing cut-away portions facilitates manufacturing of a connector where especially the insertion section and the cut-away portions are formed so that the edges of the cut-away portions are adequately smooth and chamfered to prevent damage the cuff of the endotracheal tube during insertion through the bore of the connector.

In another aspect of the invention the object is achieved by a connector for an airway tube of an artificial airway device insertable into a patient, the airway tube having a bore extending from a proximal to a distal end of the airway tube, the airway tube configured such that in use, the teeth of the patient contact the proximal end at a point of tooth contact, the connector comprising: a connector body with a longitudinal bore, a flange extending radially from the connector body, and an insertion section adapted for insertion into the bore at the proximal end of the airway tube to support the airway tube in use, the insertion section including a first continuous wall extending longitudinally from the flange, at least two wall portions extending longitudinally from the first continuous wall to a second continuous wall, and two parallel and opposite longitudinal wall cut-away portions intermediate the at least two wall portions, the at least two wall cut-away portions configured to reduce support of the airway tube for allowing local deformation of the airway tube at the point of tooth contact upon application of pressure by the patient's teeth, whilst preventing the airway tube from a full collapse.

BRIEF DESCRIPTION OF THE DRAWINGS

The invention will now be described in greater detail based on non-limiting exemplary embodiments and with reference to the drawings, on which.

DETAILED DESCRIPTION

Figure 1:
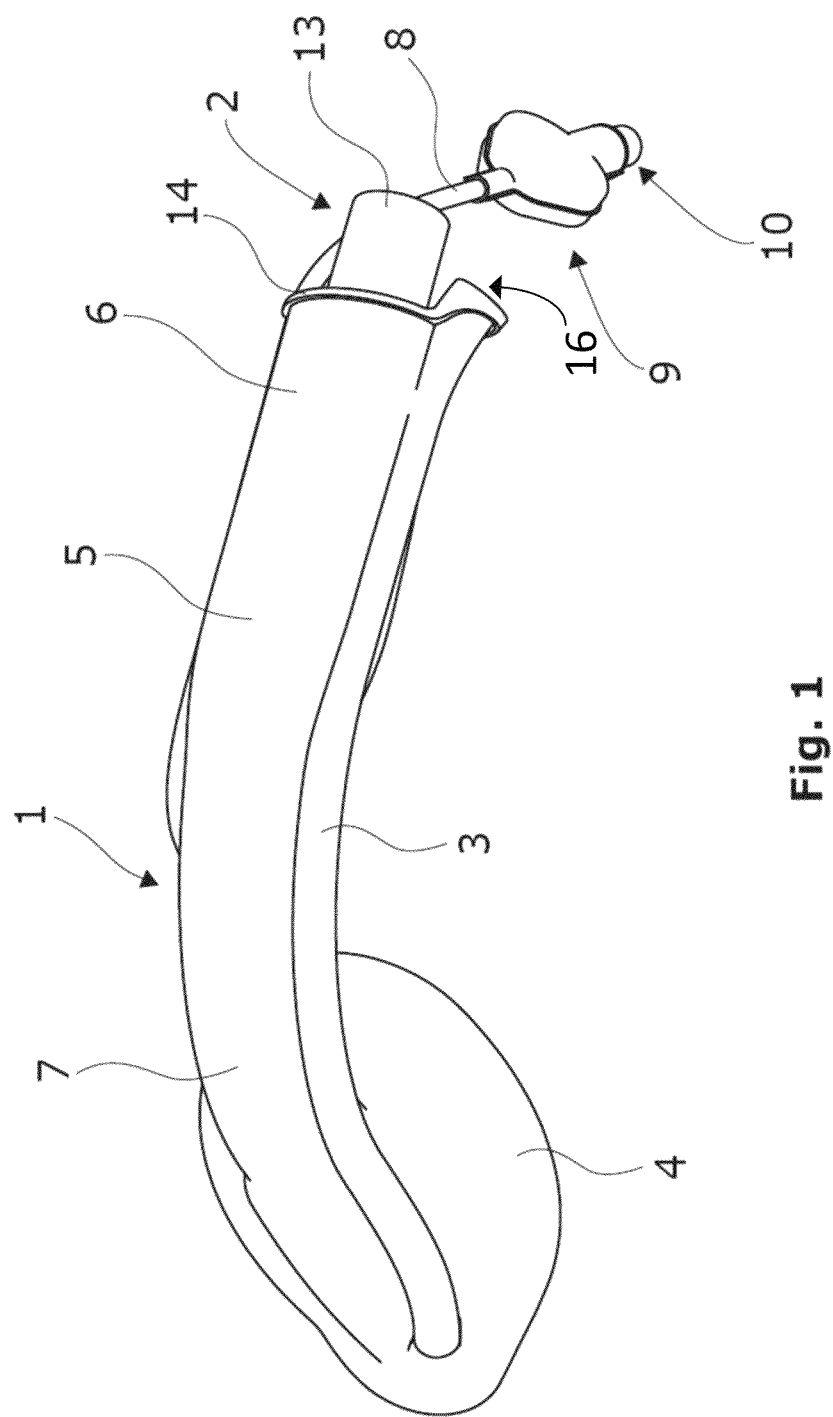
FIG. 1 shows a laryngeal mask with a connector according to the invention.

In FIG. 1 is shown a laryngeal mask 1 with a connector 2 according to an embodiment according to the invention. The laryngeal mask 1 shown is of the kind which comprises a gastric tube 3 allowing for removal of gastric matter in case of regurgitation while the laryngeal mask 1 is placed in the patient, where the laryngeal inlet of the patient is sealed by a mask portion 4 so that the patient can be ventilated via the airway tube 5. The schematically depicted laryngeal mask with the provision of a gastric tube 3 is known from now expired U.S. Pat. No. 4,995,388 and especially from U.S. Pat. No. 5,241,956. However, as will become apparent from the following description, the connector according to the invention is not limited to this specific type of laryngeal masks.

In the following description the left-hand side and the right-hand side will be understood as corresponding to the left-hand side and the right-hand side of the patient when the laryngeal mask is correctly inserted into the patient. Similar terms such as ventral and dorsal are to be understood in corresponding sense, i.e. as they would commonly be used for the patient.

As the laryngeal mask 1 is to be inserted into a patient it is preferably made of a phthalate free PVC. An airway tube 5 of the laryngeal mask 1 has a bore extending from a proximal end 6 to a distal end 7 of the airway tube 5, which terminates in an aperture surrounded by the mask portion 4. The airway tube 5 is configured such that in use, the teeth of the patient contact the proximal end at a point of tooth contact. The laryngeal mask may for instance be made of a PVC having a Shore A hardness about 48. A connector 2 preferably made of a copolyester is fitted into the proximal end of the airway tube 5. For the sake of completeness, the laryngeal mask device as also comprises an inflation tube 8, a distal end of which is in communication with the mask portion 4 for inflation thereof and a proximal end of the inflation tube terminates in a pilot balloon 9, which allows for a tactile detection of the inflation pressure of the mask portion 4. The pilot balloon 9 comprises a valve 10 adapted for insertion of the tip of a syringe for inflation and deflation of the mask portion via the pilot balloon 9 and the inflation tube 8.

Figure 2:
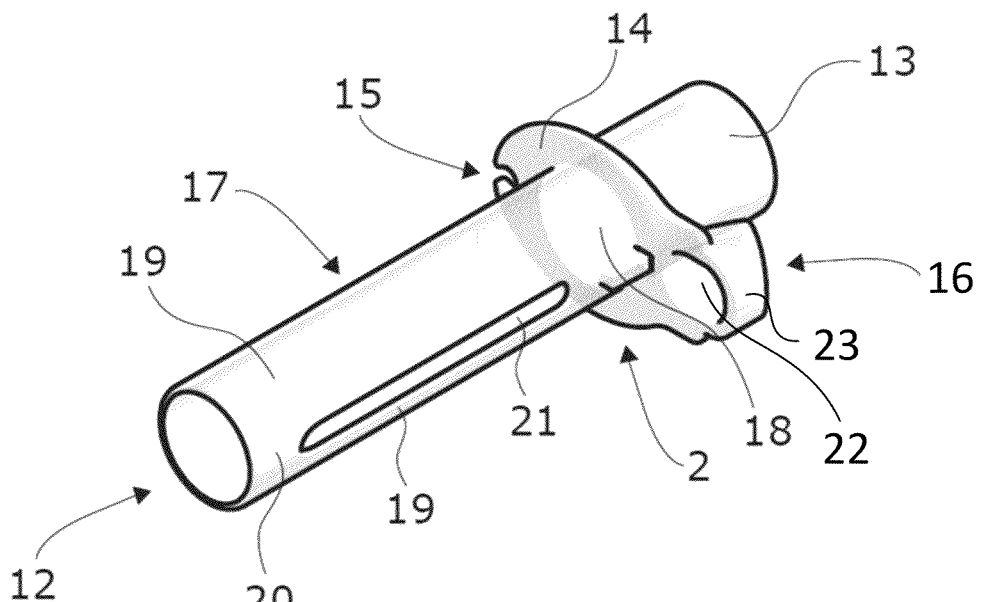
FIGS. 2 and 4 are perspective views of connector according to different embodiments of the invention.
Figure 3:
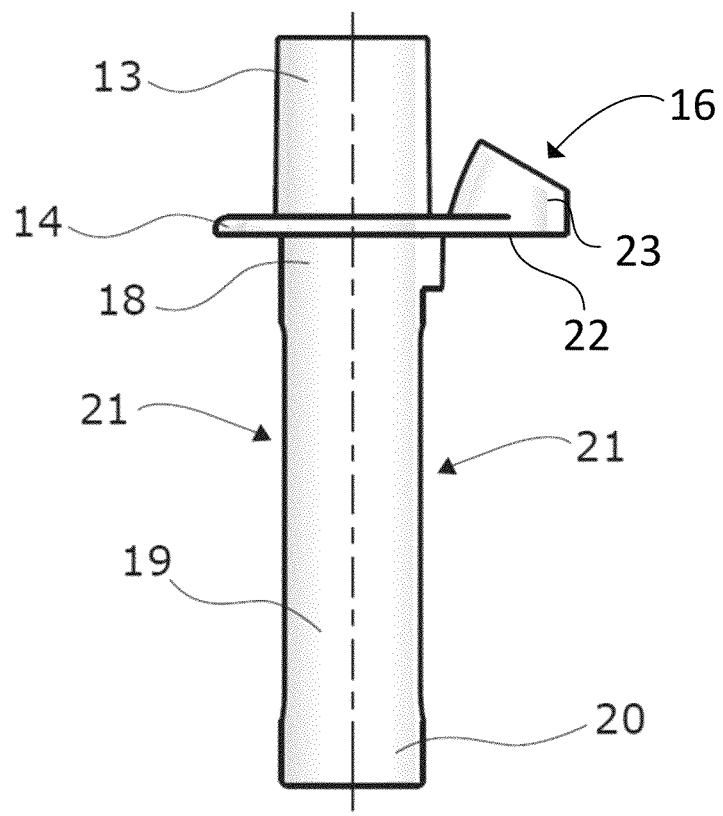
FIG. 3 is a side view of a first embodiment of the invention.
Figure 4:
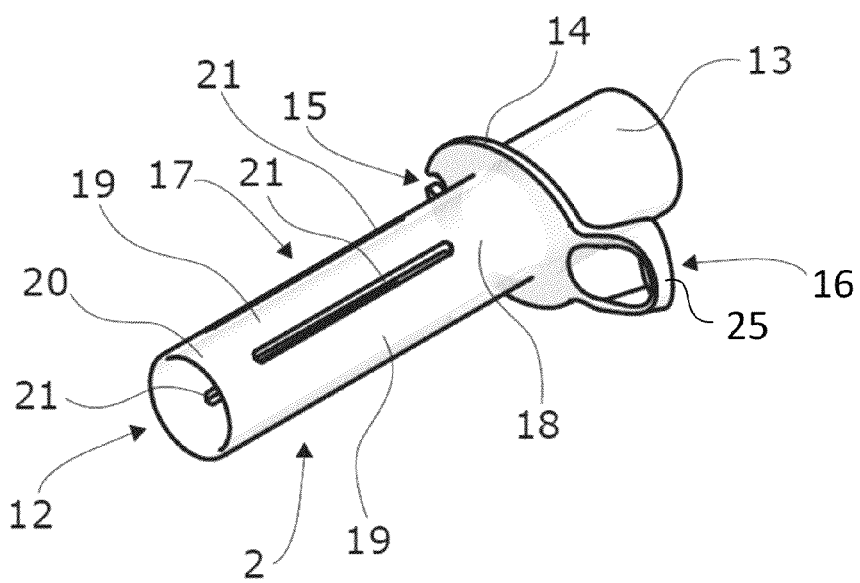

FIGS. 2 and 4 show two different embodiments of a connector 2 according to the invention. A connector 2 according to these two embodiments comprising a preferably cylindrical connector body with a longitudinal bore 12. A proximal end of the connector 2 comprises machine connector part 13 adapted to connect the laryngeal mask to a breathing apparatus. A flange 14 extends radially from the connector body and serves as a stop when the connector is inserted into the airway tube. The flange 14 may have a cut-away portion 15 adapted to releasably hold the inflation tube 8. Further, the flange 14 may have a gastric tube retention feature 16 adapted for holding and guiding the gastric tube 3. The gastrict tube retention feature 16 may comprise a bore 22, shown in FIGS. 2 and 3, and a cut-away 24, shown in FIGS. 4-6. A distal end of the connector 2 is provided with an insertion section 17 adapted for insertion into the bore at the proximal end of the airway tube 5. Thereby the insertion section 17 serves to support the airway tube 5 in use.

The insertion section 17 has a first continuous wall 18 extending longitudinally away from the flange 14 and two wall portions 19 extending longitudinally from the first continuous wall 18 to a second continuous wall 20. Two parallel and opposite longitudinal wall cut-away portions 21 forming through-going slots in the insertion section are intermediate the at least two wall portions 19. The length of the longitudinal wall cut-away portions 21 may vary in length, but is preferably greater than the length of the first continuous wall 18. In practical embodiments the first continuous wall 18 has a length about 1-2 cm from the flange 14, the length between the first continuous wall to the second continuous wall is about 3-6 cm, and the second continuous wall 20 has a length about 1-2 cm, and the width of the continuous cut-out portions 21 is about 1-3 mm. The thickness of the continuous walls 18, 20 and the wall portions 19 is about 0.8 mm. The second continuous wall 20 facilitates insertion of the insert section 17 into the airway tube 5, but also ensures a tight fit between the insertion section and the airway tube 5 making it possible to assembly only using a friction fit. This may be done by introducing the insertion section 17 into the airway tube 5 immediately after injection moulding while the airway tube is still warm from the moulding process. When the airway tube cools off it shrinks and a tight friction fit is established between the airway tube 5 and the insertion section 17 at all conditions during normal use.

The embodiment of FIGS. 2 and 3 has opposing left-hand side and right-hand side cut-away portions 21 positioned on opposing sides of a central plane defined by the ventral-dorsal direction, which is indicated by the dotted line of FIG. 3. The two opposing wall portions 19 extend longitudinally from the first continuous wall 18 to a second continuous wall 20 and are positioned towards the ventral and dorsal sides, respectively. In the present embodiment, the gastric tube retention feature 16 includes a protruding portion 23 having the bore 22 therethrough. As best shown in FIG. 3, the bore 22 begins as an opening on the flange 14. The protruding portion 23 is connected to and extends from the flange 14.

Figure 5:
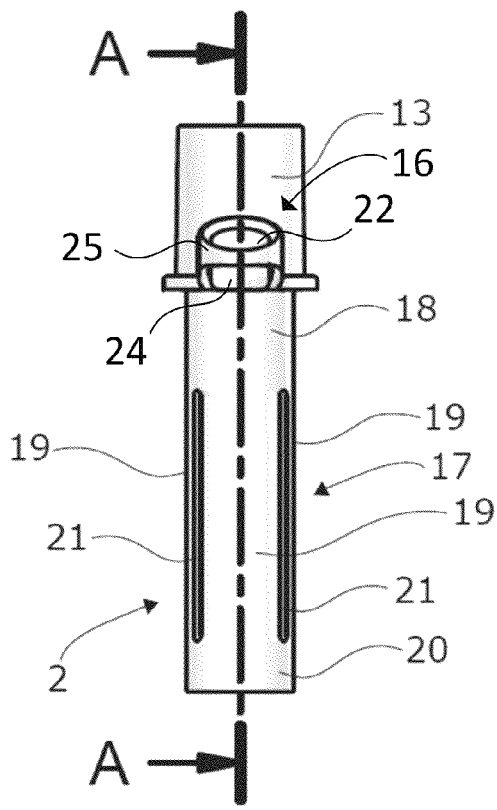
FIG. 5 is a side view of a second embodiment of the invention.
Figure 6:
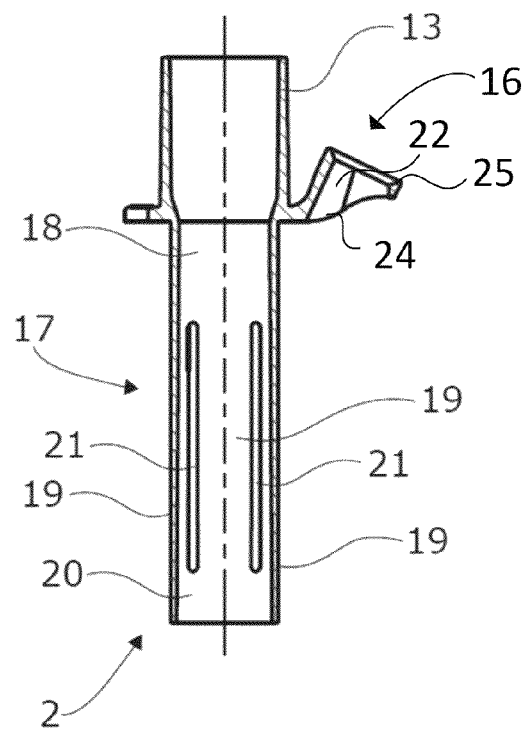
FIG. 6 is a cross sectional view of FIG. 5 taken along the line A-A.

The embodiment of FIGS. 4, 5 and 6 has two opposing cut-away portions 21 positioned on each side of opposing sides of a central plane defined by the left-right direction, which is indicated by the dotted line of FIG. 5. Hence this embodiment has a pair of two cut-away portions 21 positioned on each side of a central plane defined by the left-right direction. Hence the connector according to the embodiment of FIGS. 4-6 has four cut-away portions 21 and four wall portions 19, where two of the wall portions are lateral left-hand side and right-hand side wall portions and two of the wall portions 19 are dorsal side and ventral side wall portions 19.

FIG. 6 is a cross-sectional view along the line A-A of FIG. 5 and shows the two cut-away portions 21 positioned towards on the ventral side, i.e. the right-hand side cut-away portion 21 shown in FIG. 5 corresponds to the right-hand side cut-away portion 21 shown in FIG. 6. The dotted line of FIG. 6 illustrates the central ventral-dorsal plane. In the present embodiment, the gastric tube retention feature 16 includes the cut-away 24 in the flange 14 and a protruding portion 25 connected to and extending from the flange 14.

Generally, the wall cut-away portions are configured to reduce support of the airway tube 5 where the insertion section 17 is present for allowing local deformation of the airway tube at the point of tooth contact upon application of pressure by the patient's teeth, whilst preventing the airway tube from a full collapse. Hence, the configuration with at least two cut-away portions allows for a substantial deformation of the airway tube 5 at the point of tooth contact so that the connector functions as a bite absorber. The airway tube 5 and the connector 2 according to the invention are configured so that the point of tooth contact during use is located between the first continuous wall 18 and the second continuous wall 20. Evidently, the shape of the through-going slots forming the cut-away portions 21 may take many shapes and need not to extend directly from the first continuous all 18 to the second continuous wall 20, i.e. the cut-away portions 21 may for instance furcate and be spiral shaped.

Since the connector according to the invention is not an integral part of the airway tube, it will require no or only a very limited modification of the design of the airway tube, and therefore the connector according to the invention may easily be implemented in existing laryngeal mask designs where the advantages of the invention may be appreciated.

The invention claimed is:

1. A laryngeal mask insertable into a patient, the laryngeal mask comprising:
    an airway tube having a bore extending from a proximal to a distal end of the airway tube, the airway tube configured such that in use, patient's teeth contact the proximal end at a point of tooth contact,
    a mask portion connected to the distal end of the airway tube,
    a gastric tube having a proximal end opposite a distal end, the gastric tube positioned external and adjacent the airway tube with the distal end of the gastric tube connected to the mask portion, and
    a connector affixed to the proximal end of the airway tube in a fixed predetermined orientation, the connector comprising:
        a connector body with a longitudinal bore having a longitudinal axis,
        a flange extending radially from the connector body,
        a gastric tube retention feature comprising one of a cut-away and a bore, the gastric tube retention feature configured to retain the proximal end of the gastric tube, and
        an insertion section inserted into the bore of the airway tube to support the airway tube in use, the insertion section including
            a first continuous wall extending longitudinally from the flange,
            at least two wall portions extending longitudinally from the first continuous wall to a second continuous wall, and
            two parallel and opposite longitudinal wall cut-away portions intermediate the at least two wall portions, the length of each of the two cut-away portions being greater than the length of the first continuous wall, the two cut-away portions and the at least two wall portions configured to allow local deformation of the at least two wall portions and the airway tube at the point of tooth contact upon application of pressure by the patient's teeth, whilst preventing the airway tube from a full collapse.

2. A laryngeal mask according to claim 1, wherein the two cut-away portions are positioned on opposing sides of a ventral-dorsal plane of the laryngeal mask.

3. A laryngeal mask according to claim 2, wherein the two cut-way portions are positioned on a left-right plane of the laryngeal mask.

4. A laryngeal mask according to claim 2, wherein the two cut-away portions are positioned on opposing sides of a left-right plane of the laryngeal mask.

5. A laryngeal mask according to claim 4, wherein the insertion section comprises four cut-away portions, the four cut-away portions including the two cut-away portions, wherein two of the four cut-way portions are positioned on each side of the left-right plane of the laryngeal mask.

6. A laryngeal mask according to claim 1, wherein the two cut-away portions are positioned on opposing sides of a left-right plane of the laryngeal mask.

7. A laryngeal mask according to claim 1, wherein the insertion section comprises four cut-away portions, the four cut-away portions including the two cut-way portions, wherein two of the four cut-away portions are positioned on each side of a left-right plane of the laryngeal mask.

8. A laryngeal mask according to claim 1, wherein an internal surface of the airway tube defines the bore, and wherein the at least two wall portions contact the internal surface of the airway tube.

9. A laryngeal mask according to claim 1, the gastric tube retention feature comprising the cut-away and further comprising a protruding portion connected to the flange and extending from the cut-away.

10. A laryngeal mask according to claim 9, the protruding portion comprising the bore therethrough.

11. A laryngeal mask according to claim 1, the gastric tube retention feature comprising the bore, the bore having an opening located on the flange, and the gastric tube retention feature further comprising a protruding portion connected to the flange and extending from the opening.

12. A connector for an airway tube of an artificial airway device insertable into a patient, the airway tube having a bore extending from a proximal to a distal end of the airway tube, the airway tube configured such that in use, patient's teeth contact the proximal end at a point of tooth contact, the connector comprising:
    a connector body with a longitudinal bore having a longitudinal axis,
    a flange extending radially from the connector body,
    a gastric tube retention feature comprising one of a cut-away and a bore, the gastric tube retention feature being adjacent the connector body and adapted to retain a proximal end of a gastric tube positioned external and adjacent the airway tube, and
    an insertion section adapted for insertion into the bore of the airway tube at the proximal end thereof to support the airway tube in use, the insertion section including
        a first continuous wall extending longitudinally from the flange,
        at least two wall portions extending longitudinally from the first continuous wall to a second continuous wall, and
        two parallel and opposite longitudinal wall cut-away portions intermediate the at least two wall portions, the two cut-away portions and the at least two wall portions configured to allow local deformation of the at least two wall portions and the airway tube at the point of tooth contact upon application of pressure by the patient's teeth, whilst preventing the airway tube from a full collapse.

13. A connector according to claim 12, wherein the two cut-away portions are positioned on opposing sides of a ventral-dorsal plane of the artificial airway device.

14. A connector according to claim 13, wherein the two cut-way portions are positioned on a left-right plane of the artificial airway device.

15. A connector according to claim 13, wherein the two cut-away portions are positioned on opposing sides of a left-right plane of the artificial airway device.

16. A connector according to claim 15, wherein the insertion section comprises four cut-away portions, the four cut-away portions including the two cut-away portions, wherein two of the four cut-way portions are positioned on each side of the left-right plane of the artificial airway device.

17. A connector according to claim 12, wherein the two cut-away portions are positioned on opposing sides of a left-right plane of the artificial airway device.

18. A connector according to claim 12, wherein the insertion section comprises four cut-away portions, the four cut-away portions including the two cut-away portions, wherein two of the four cut-way portions are positioned on each side of a left-right plane of the artificial airway device.

19. A connector according to claim 12, wherein the length of each of the two cut-away portions is greater than the length of the first continuous wall.

20. A connector according to claim 12, wherein the insertion section comprises a cylindrical external surface configured to contact an internal surface of the bore of the airway tube, and the at least two wall portions have a thickness of about 0.8 mm.

21. A connector according to claim 12, the gastric tube retention feature comprising the cut-away and further comprising a protruding portion connected to the flange and extending from the cut-away.

22. A connector according to claim 21, the protruding portion comprising the bore therethrough.

23. A connector according to claim 12, the gastric tube retention feature comprising the bore, the bore having an opening located on the flange, and the gastric tube retention feature further comprising a protruding portion connected to the flange and extending from the opening.

* * * * *